United States Patent [19]

Pero

[11] Patent Number: 5,340,565
[45] Date of Patent: Aug. 23, 1994

[54] TUMOR OR CANCER CELL KILLING THERAPY AND AGENTS USEFUL THEREFOR

[75] Inventor: Ronald W. Pero, New York, N.Y.

[73] Assignee: Oxi-Gene, Inc., New York, N.Y.

[21] Appl. No.: 896,236

[22] Filed: Jun. 10, 1992

Related U.S. Application Data

[63] Continuation of Ser. No. 89,477, Aug. 25, 1987.

[51] Int. Cl.$^5$ .................... A61K 49/00; G01N 33/15
[52] U.S. Cl. ........................ 424/10; 424/649
[58] Field of Search .................. 424/10, 649; 514/619

[56] References Cited

U.S. PATENT DOCUMENTS 5,081,153 1/1992 Pathak et al. .................. 424/649

OTHER PUBLICATIONS

White et al., "Induction Chemotherapy for Advanced Head and Neck Cancer . . . ," Am. J. Clin. Oncol. (CCT), 15(1) (1992), pp. 45–55.
S. Lybak et al., "Dose schedule evaluation of metoclopramide . . . ," Anti–Cancer Drugs 2: 375-82 (1991).
R. J. Nelt et al., "Phamacokinetis of Non––Protein–Bound Platinum Species . . . ," Cancer Treat. Rep. 63: 1515-21 (1979).
J. Hansson et al., "Cis–Diamminedichloroplatinum (II) Toxicity . . . ," Acta Oncologica 27: 383-92 (1988).
K. C. Micetich et al., "A Comparative Study of the Cytotoxicity . . . ," Cancer Research 45: 4043-47 (1985).
L. A. Zwelling et al., "DNA–Protein and DNA Interstrand Cross–Linking . . . ," Cancer Research 39: 365-69 (1979).
C. A. Perez et al., "Impact of Irradiation Technique and Tumor Extent . . . ," Cancer 50: 1091-99 (1982).
E. Kjellen et al., "Metoclopramide enhances the effect of cisplatin . . . ," Br. J. Cancer 59: 247-50 (1989).
E. Kjellen et al., "A therapeutic benefit from combining normobaric carbogen . . . ," Radiotherapy and Oncology 22: 81-91 (1991).
S. Lybak, Metoclopramide: A representative of a new class of drugs for potentiation of cytotoxicity, University of Lud, Sweden (1991), p. 115.

Primary Examiner—Nathan M. Nutter
Attorney, Agent, or Firm—Cooper & Dunham

[57] ABSTRACT

The effectiveness of cytostatic and/or cytotoxic drugs and/or radiation in the killing of tumor and/or cancer cells is increased by the administration, along with said drugs and radiation, of an effective activating or inhibiting amount of a compound or agent which activates or inhibits the chromatin-bound enzyme adenosine diphosphate ribosyl transferase (ADPRT) or the administration of an effective intracellular free $Ca^{++}$-increasing amount of a compound which induces cellular or oxidative stress or which acts as an inhibitor or antagonist or calmodulin or $Ca^{++}$-calmodulin binding. Suitable such compounds or agents include the phenothiazines, antihistamines, butyrophenones, cannabinoids and corticosteriods and particularly metoclopramide when employed in combination with cisplatin.

7 Claims, 1 Drawing Sheet

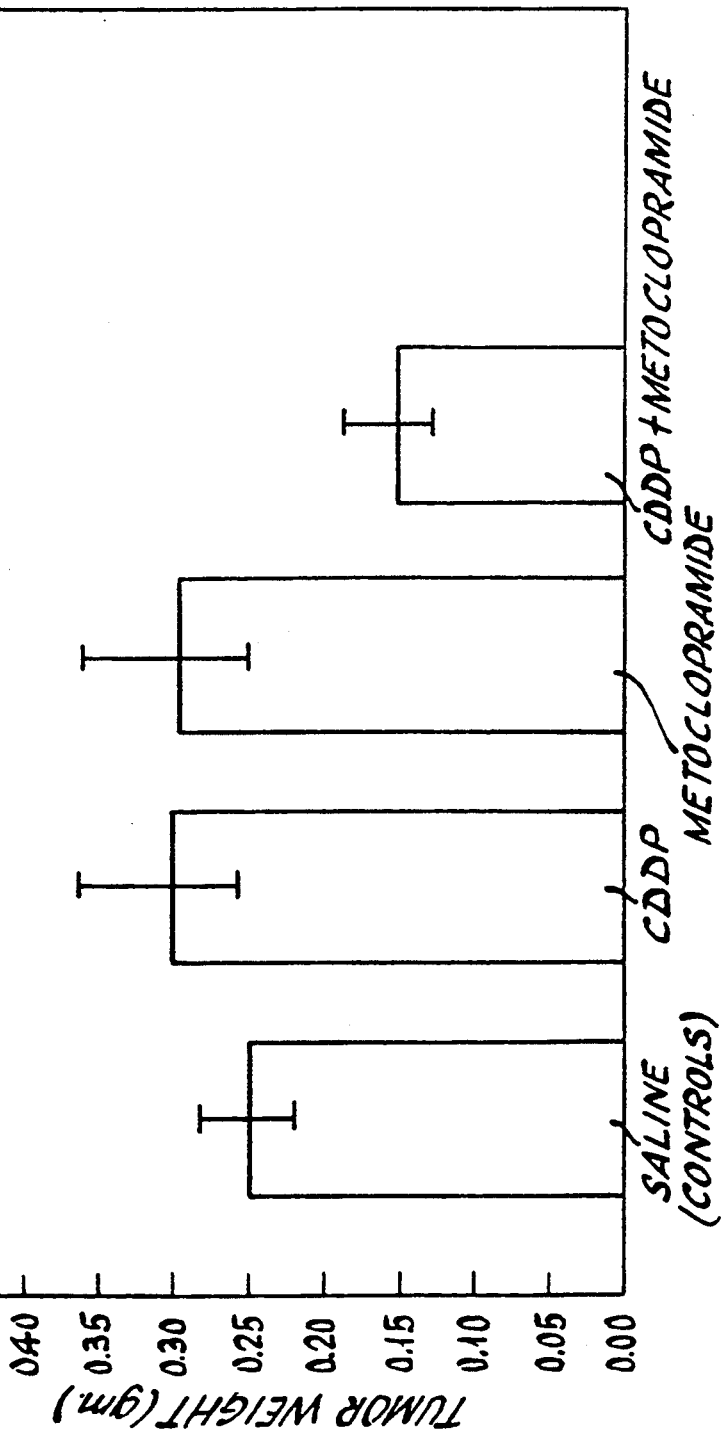

TUMOR OR CANCER CELL KILLING THERAPY AND AGENTS USEFUL THEREFOR

This is a continuation of application Ser. No. 089,477, filed Aug. 25, 1987.

BACKGROUND OF THE INVENTION

One important strategy in designing effective cancer chemotherapeutic drugs is defining the mechanism of cell death. Activation of the chromatin-bound enzyme, adenosine diphosphate ribosyl transferase (ADPRT), and the subsequent depletion of energy metabolites, such as NAD and ATP, are involved in the suicidal response to induced cellular DNA damage that leads eventually to cell death, Berger, N. A., J. Clin. Invest. 78:1131–1135, 1986.

Radiation and/or most cancer therapeutic drugs induce DNA damage, and as a consequence involve ADPRT activity as part of their cytotoxic mechanisms of action, Huet and Laval, Int. J. Radiat. Biol. 47: 655–662, 1985.

Hence, inducers of ADPRT enhance cytotoxicity by seriously depleting cellular energy pools in an effort to repair the potentially lethal DNA damage induced by most chemotherapeutic drugs and/or radiation. This is true because NAD is consumed as a co-substrate by ADPRT activity, Hayaishi and Ueda, Ann. Rev. Biochem. 46:96–116, 1977; Purnell et al, Biochem. Soc. Trans. 8:215–227, 1980, which is in turn, induced by DNA strand breaks, Halldorsson et al. FEBS Lett. 85:349–352, 1978; Benjamin and gill, J. Biol, Chem. 255:10493–10508, 1980; Cohen and Berger, Biochem. Biophys. Res. Commun. 98: 268–274, 1981. Since cellular NAD/ATP pools are coupled, then cellular energy is depleted and cytotoxicity is enhanced. On he other hand, inhibitors of ADPRT are also sensitizers of cytotoxicity because they prevent the repair of potentially lethal DNA damage.

BRIEF DESCRIPTION OF THE DRAWING

FIG. 1 shows the effect of treatment of the growth of a human squamous cell carcinoma xenographed to nude mice with CDDP (CiS-Diamine-Dichloroplatinum) combined with Metoclorpramide.

The invention is indicated in accompanying FIG. 1 wherein data demonstrating the effectiveness of a practice of this invention is graphically illustrated.

SUMMARY OF THE INVENTION

This invention relates to the discovery that many compounds with antiemetic action, such as the substituted N-tertiary amino benzamides, phenothiazines, antihistamines, butyrophenones, cannabinoids, and corticosteriods have properties that enhance the effectiveness of cytostatic drugs or radiation in the killing of tumor cells. Broadly, compounds which activate or inhibit the chromatin-bound enzyme adenosine diphosphate ribosyl transferase ADPRT or which induce cellular or oxidative stress or which act as inhibitors or antagonists of calmodulin or $Ca^{++}$-calmodulin binding are useful to enhance the effectiveness of cytostatic drugs or radiation in the killing of tumor cells.

DETAILED DESCRIPTION OF THE INVENTION

There are at least 4 well known classes of inhibitors of ADPRT; namely nicotinamide analogs, benzamide analogs, pyrazinamide analogs and purine analogs, Sims et al, Biochem. 21: 1813–1821, 1982, Nduka et al, Eur. J. Biochem. 105: 525–530, 1980. The common structural feature that was shown to be of importance to maintain a high degree of inhibition of ADPRT by the analogs of nicotinamide, benzamide and pyrazinamide, is the presence of a ring-carboxamide group. For example, benzoic acid, 3-aminobenzoic acid, pyrazine 1,2-dicarboxylic acid, isonicotinic acid, and 6-amino nicotinic acid all failed to inhibit ADPRT, Sims et al, Biochem. 21:1813–1821, 1982. Therefore, judging from an experimental point of view it would not be obvious that N-tertiary amino substitutions of the carboxamide residue of benzamide analogs would result in derivatives that can modulate ADPRT. In fact, the only known pharmacological/biological effects reported in the scientific literature for these analogs are as antiemetic agents, see U.S. Pat. No. 3,177,252, and for review see also Weiss and Weintraub, Drug Ther. 12:167–170, 1982 and Reich, S. O., Cancer Nurs. 6:71–73, 1983).

Nicotinamide, benzamide, 3-aminobenzamide and purine analogs, such as theophylline and other xanthines, have been shown to be effective sensitizers of the cytotoxic action induced by radiation and cancer chemotherapeutic drugs in both cell culture and animal tumor model systems, Ben-Hur, E., Int. J. Radiat. Biol. 46:659, 1984; Utsumi and Elkind, Brit. J. Cancer (suppl. 6):39, 1984; Calcutt et al, Brit. J. Cancer 24:380, 1970; George et al, Int. J. Radiat. Biol. 49:783, 1986; Thraves et al, Int. J. Radiat. Oncol. Biol. Phys. 12:1541, 1986; Thraves et al, Radiat. Res. 104:119, 1985; Thraves et al, Int. J. Radiat. Biol. 50:961, 1986; Kumar et al, Int. J. Radiat. Biol. 47:103, 1985; Huet and Laval, Int. J. Radiat. Biol. 47:655, 1985; Jonsson et al, Cancer Res. 45:3609, 1985; Kjelle'n et al, Acta Radiologica 25:281, 1986; Horsman et al, Int. J. Radiat. Oncol. Biol. Phys. 12:1307, 1986; Horsman et al, Radiat. Res. 109:479, 1987; Nduka et al, Eur. J. Biochem. 105:525, 1980; Mourelatos et al, Mutation Res. 121:147, 1983. However, with the exception of nicotinamide, all of these classes of sensitizers are quite toxic by themselves thereby limiting their potential development for use in humans. Furthermore, relatively high doses were required for sensitizing either cells (millimolar concentration) or tumor bearing animals (>100 mg/kg) to radiation or cancer chemotherpeutic drugs.

Nicotinamide will radiosensitize an adenocarcinoma transplanted in C3H mice at a dose of 10 mg/kg whereas benzamide is totally ineffective in this dose range, Kjelle'n and Pero, Eight International Symposium on ADP-ribosylation, May 30-Jun. 3, 1987, Forth Worth, Tex., Abstract 76. The low dose effectiveness of nicotinamide has been attributed to an active transport mechanism for which benzamide can only partially and poorly compete, Pero et al, Eight International Symposium on ADP-ribosylation, May 30-Jun. 3, 1987, Forth Worth, Tex., Abstract 69. However, compounds which would compete for the nicotinamide binding and transport site and which modulate ADPRT, then such compounds would be theoretically effective sensitizers of radio-and chemotherapies at non-toxic low doses. Metoclopramide (4-amino-5-chloro-N-[(2-diethylamino)ethyl]-2-methoxy-benzamide) is a drug like nicotinamide in that it sensitizes a cancer chemotherapeutic agent at the daily low dose of 2 mg/kg.

Most chemotherapeutic agents utilized in the treatment of tumors cause, among other disturbances, a gastrointestinal toxicity characterized in particular by nausea and vomiting. These symptoms are important in that they affect the patients' well-being and ability to nourish themselves and often may exercise an influence on their acceptance or refusal to continue treatment. Metoclopramide is well established as a successful antiemetic treatment for chemotherapy induced nausea and vomiting, see Reich, S. D. Cancer Nurs. 6:71–73, 1983, although several other drugs with antiemetic properties, such as phenothiazines, antihistamines, benzamide derivatives, butyrophenones, cannabinoids, and corticosteriods have been used, Laszlo, J. Drugs 25 (Suppl. 1):1–7, 1983. However, despite the common use of metoclopramide and other antiemetics in chemotherapeutic treatment regimens, these drugs have never been evaluated in relation to the clinical effectiveness of the chemotherapeutic drug and in combination therewith.

Contrary to scientific expectations and based on benzamide analog studies as inhibitors of ADPRT and thus sensitizers of radio- and chemo- therapies, substitutions into the carboxamide group of benzamide, nicotinamide and pyrazinamide analogs, do not necessarily destroy the sensitizing properties of these compounds since metoclopramide, a polysubstituted-N-tertiary amino alkyl benzamide, is an effective sensitizer in cancer chemotherapy, such as a sensitizer of a cancer chemotherapeutic drug.

The following are examples of the practices of this invention.

EXAMPLE I

Cisplatin (cis-diamine-dichloroplatinum=CDDP) is a heavy metal complex with alkylating properties which allow bifunctional linking to DNA. CDDP has been used successfully as a chemotherapeutic agent to treat several types of human cancers. Since CDDP treatment regimes induce nausea and vomiting, metoclopramide is often co-administered therewith as an antiemetic drug. This example demonstrates that metoclopramide not only suppresses the number of episodes of nausea and vomiting, but it also potentiates the cytotoxic effect of CDDP on human cancer cells, such as on a human squamous cell carcinoma (SCC) (ABII) of the head and neck xeno-grafted to nude mice.

Two administration schedules were tested: (A) metoclopramide (2.0 mg/kg i.p.) one hour before CDDP (7.5 mg/kg i.p.) and (B) metoclopramide (2.0 mg/kg×3 treatment times) given separately concomitant to CDDP (7.5 mg/kg i.p.) and 24 hr and 48 hr after CDDP administration. In both schedules the combined treatment was compared with CDDP alone, metoclopramide alone and with physiologic saline treated tumor bearing animals (controls). The tumor line used was a poorly differentiated human SSC originating from the nose. There were n=10 animals in each group. Tumor diameters and animal weight were recorded and plotted twice weekly for 21 days. Treatment efficacies were compared using the area under the plotted growth curves (AUC).

There was no mortality and no weight loss of significance in any treatment group. In neither schedule A nor B did metoclopramide alone induce any significant reduction in AUC. CDDP alone gave a significant reduction of AUC-values. In schedule A the addition of metoclopramide did not give any additive effect. In schedule B metoclopramide potentiated the effect of CDDP, which when given alone reduced AUC to 72% of control tumor growth. CDDP+metoclopramide significantly reduced AUC to 36% of control tumor growth. The above experiment was repeated using another human SSC (EH) transplanted in nude mice. The tumor weights at day 21 after the initiation of the experiment are graphically presented in FIG. 1. Likewise, a significant reduction in tumor weight was achieved with a combined treatment of CDDP+metoclopramide. These data show that metoclopramide sensitizes or enhances the cytotoxic action of CDDP against two different human SSC lines carried in nude mice, and at a dose currently being administered as an antiemetic agent to patients receiving cancer chemotherapy.

As mentioned above, inhibitors of ADPRT enhance the cytotoxicity induced by radiation and cancer chemotherapeutic drugs. However, it is also important to appreciate that DNA strand damaging agents induce ADPRT activity and DNA damage is a target site for the biological induction of cytotoxicity, Durkacz et al, Nature 296: 593–596, 1980, and as cited above. Therefore, both inhibitors and inducers of ADPRT are potential sensitizers of the cytotoxic action of drugs, e.g. (A) inhibitors because they prevent the removal of potentially lethal DNA damage by ADPRT directed DNA repair mechanisms and (B) inducers because they enhance the production of drug- or radiation-induced DNA damage by altering the endogenous cellular mechanisms that lead to DNA damage and the subsequent activation of ADPRT. The following example presents one such mechanism of endogenous DNA damage induction valid in general for many of the drugs with antiemetic properties.

The free cytosolic level of $Ca^{++}$ is known to be a critical event in the mechanism of cytotoxicity, Trump and Berezesky, Role of Sodium and Calcium Regulation in Toxic Cell Injury, in Drug Metabolism and Drug Toxicity, J. R. Mitchell and M. G. Horning (eds), Raven Press, New York, pp 261–300, 1984, and agents that induce oxidative stress increase intracellular free $Ca^{++}$ which is, in turn, modulated by the $Ca^{++}$ binding protein calmodulin, Mirabelli et al, J. Biochem. Toxicol. 1: 29–39, 1986; and Means and Dedman, Nature 285: 73–77, 1980. Hence, antagonists of $Ca^{++}$-calmodulin binding or agents that increase free cytosolic $Ca^{++}$, such as oxygen radicals produced by oxidatively stressing the cell, would be expected to increase DNA damage, thereby activating ADPRT and inducing cytotoxicity by a mechanism different from that associated with an inhibition of ADPRT and DNA repair, Schraufstatter et al, J. Clin. Invest. 76: 1131–1139, 1985, and Schraufstatter et al, J. Clin. Invest. 77: 1312–1320, 1986.

The following Example II establishes that many antiemetic agents can modulate cellular $Ca^{++}$ homeostasis, activate ADPRT, induce cytotoxicity in themselves and thus possess the properties to sensitize or enhance or increase cytotoxicity when used in combination with radiation and/or cancer chemotherapy drugs. Although some antiemetic agents are known to antagonize $Ca^{++}$-calmodulin binding, Hidaka H. and Hartshorne D. J. (eds) Calmodulin Antagonists and Cellular Physiology, Academic Press, Inc. New York, pp. 1–543, 1985), they are not known to induce ADPRT or to enhance cytotoxicity.

EXAMPLE II

Human mononuclear leukocytes (HML) were isolated by Isopaque-Ficoll gradient centrifugation from heparinized peripheral blood samples as already described, (Boyum, A., Scand. J. Clin. Lab. Invest. 21

(Suppl. 7): 7, 1968. The HML were adjusted to $1 \times 10^6$ cells per ml of Eagles minimum essential medium and cultured at 37° C. for 30 min in the presence or absence of the indicated doses of the compounds shown in accompanying Table 1. Either physiologic saline or 95% ethanol (>0.5%, v/v) were used as co-solvents. Cytotoxicity was assessed by trypan blue exclusion either after the 30 min incubation period or after 18 hr incubation at 37° C. of parallel cultures as already described, Pero et al, Mutation Res. 83:271-289, 1981. ADPRT activity was always estimated after the 30 min of exposure and incubation in permeabilized cells as described previously, Pero et al, Chem. Biol. Interactions 47:265-275, 1983. Briefly, HML were permeabilized, exposed to 250 µM NAD tritium-labelled in the adenine moiety (20-25 Ci/mMol, Amersham; diluted 875:1 with cold NAD) for 15 min at 30° C., and the protein-bound ADP-ribose collected onto nitrocellulose filters following precipitation with 10% trichloroacetic acid (TCA). The data were recorded as cpm TCA precipitable [$^3$H]NAD per $1 \times 10^6$ cells.

W-7, see footnote to Table 1, is a well characterized calmodulin antagonist which has an IC$_{50}$ dose of around 50 µM whereas W-5, a closely related structural analog, is inactive at 50 µM and it has a IC$_{50}$ of about 250 µM Hidaka et al, Proc. Natl. Acad. Sci. U.S.A. 78:4354-4357, 1981. These two compounds have been used effectively to distinguish calmodulin modulated biological events, e.g. inhibition of cell proliferation, phosphodiesterase and myosin light chain kinase. Hence, W-7 and W-5 were used to determine the effect of calmodulin mediated cellular events on ADPRT activity and cytotoxicity. The data in accompanying Table 1 clearly show that W-7 induces ADPRT activity and this effect is paralleled by an increase in cytotoxicity. No such effects were observed with W-5, indicating that Ca$^{++}$-calmodulin antagonism is an important endogenous mechanism for mediating cytotoxic responses and cytotoxicity can be induced by agents that antagonize Ca$^{++}$-calmodulin binding.

TABLE I

Activation of ADPRT and resultant cytotoxicity induced by agents that modulate Ca$^{++}$ homeostasis in HML.

| Agents | Concentration (µM) | ADPRT Activity[a] | % Dead Cells[a] 30 min | 18 hr |
|---|---|---|---|---|
| (1) Controls | 0 | 385 | <5% | <5% |
|  | 0 | 350 | <5% | <5% |
| (2) W-7[b] | 50 | 750 | 10% | — |
|  | 100 | 910 | 25% | — |
|  | 200 | 1480 | 90% | — |
| (3) W-5[c] | 50 | 395 | <5% | — |
|  | 100 | 415 | <5% | — |
|  | 200 | 425 | 7% | — |
| (4) H$_2$O$_2$ | 100 | 1800 | 5% | 40% |
|  | 300 | 2700 | 5% | 41% |
|  | 500 | 2900 | 7% | 55% |
|  | 1000 | 3000 | 12% | 71% |
| (5) Metoclopramide[d] | 500 | 530 | 7% | 8% |
|  | 2000 | 703 | 13% | 29% |
|  | 5000 | 950 | 10% | 58% |
|  | 10000 | 870 | 22% | 88% |
| (6) Chlorpromazine[e] | 100 | 1508 | 50% | — |
|  | 500 | 890 | 100% | — |
| (7) Trimeprazine[f] | 100 | 639 | 7% | — |
|  | 500 | 571 | 95% | — |
| (8) Dixyrazine[g] | 100 | 385 | 13% | 78% |
|  | 500 | 850 | 79% | 100% |
| (9) Haloperidol[h] | 100 | 655 | 6% | — |
|  | 500 | 746 | 60% | — |
| (10) Moperone[i] | 100 | 529 | 5% | — |
|  | 500 | 712 | 7% | — |
| | 1000 | 1112 | 26% | 100% |

[a]The average of duplicate determinations are presented
[b]W-7 = N-(6-aminohexyl)-5-chloro-1-naphthalenesulfonamide
[c]W-5 = N-(6-aminohexyl)-naphthalenesulfonamide
[d]Metoclopramide = 4-amino-5-chloro-N-[(2-diethylamino)ethyl]-2-methoxybenzmide
[e]Chlorpromazine = 2-chloro-N,N-dimethyl-10H-phenothiazine-10-propanamine
[f]Trimeprazine = 10-[3-(dimethylamino)-2-methylpropyl]-10H-phenothiazine
[g]Dixyrazine = 2-[2-[4-[2-(3,3-dimethyl-1-butenyl)-10H-phenothiazin-10-yl]-ethyl]-1-piperazinyl]ethoxy]-ethanol
[h]Haloperidol = 4-[4-(4-chlorophenyl)-4-hydroxy-1-piperidinyl]-1-(4-fluorophenyl)-1-butanone
[i]Moperone = 1-(4-fluorophenyl)-4-[4-hydroxy-4(4-methyl phenyl)-1-piperidinyl]-1-butanone The importance of cellular Ca$^{++}$ homeostasis in the induction of ADPRT and cytotoxicity is further supported by the data recorded for H$_2$O$_2$ in Table 1. H$_2$O$_2$ is well known to induce a Ca$^{++}$ efflux from plasma membranes and mitochondria thus elevating intercellular free Ca$^{++}$, imbalancing Ca$^{++}$ homeostasis and inducing cytotoxicity, Mirabelli et al, J. Biochem. Toxicol. 1:29-39, 1986. Again the data clearly indicate that H$_2$O$_2$ induces ADPRT which is paralleled by increases in interphase cell death, although the cytotoxicity is more evident after 18 hr incubation than immediately after exposure (i.e. 30 min). The data confirm that agents which interfere with Ca$^{++}$ homeostasis can also enhance cytotoxicity, and therefore these types of compounds are potential sensitizers of radiation and chemotherapeutic drugs.

The data reported in Table 1 on metoclopramide confirm this hypothesis. The data reported in Example I demonstrate that metoclopramide is a good sensitizer of the chemotherapeutic drug, cisplatin, and Table 1 establishes that metoclopramide activates ADPRT and induces cytotoxicity endogenously without the addition of other cytostatic agents. Since the other classes of agents presented in Table 1 are known modulators of Ca$^{++}$ homeostasis and they, in turn, gave similar patterns of induction of ADPRT and cytotoxicity, it is concluded that these common biochemical/biological effects are characteristic of a new class of sensitizers of radiation and chemotherapeutic drugs, all as described herein. These common biochemical/biological effects are characteristic of a new class of sensitizers of radiation and chemotherapeutic drugs and are totally unexpected since metoclopramide is a benzamide derivative and benzamide derivatives have previously only been shown to sensitize cytostatic agents by inhibition of ADPRT. Consequently, Example II reveals that many antiemetic agents possess the common property of inducing ADPRT and cytotoxicity presumably via modulation of Ca$^{++}$ homeostasis thus giving these agents the potential to sensitize the cytostatic action of other agents, such as radiation and chemotherapeutic drugs.

Compositions useful in the practices of this invention include in their make-up a cytotoxic or cytostatic compound or agent and a compound or agent which activates or inhibits ADPRT and/or which induces cellular or oxidative stress, such as a compound which produces or yields cellular H$_2$O$_2$ or which acts as an inhibitor or antagonist of calmodulin or Ca$^{++}$-calmodulin binding.

Useful cytotoxic or cytostatic compounds or agents include, in addition to cisplatin, the other useful chemotherapeutic cytotoxic agents employed in cancer chemotherapy, such as adriamycin, 5-fluorouracil, methotrexate, cytoxan, vincristine, daunomycin, BCNU, CCN, MeCCNU and others.

Useful compounds or agents which activate or inhibit ADPRT or which induce cellular or oxidative stress or which act as inhibitors or antagonists of calmodulin of $Ca^{++}$-calmodulin binding include metoclopramide, chlorpromazine, trimeprazine, dixyazine, halperidol, moperone, W-7 and W-5. The recently discovered parathyroid hormone factor, PTH-like peptide, a factor which induces high blood levels of calcium, see Science, Vol. 237, pages 363,364, Jul. 24, 1987, also is usefully employed in compositions of and in the practices of this invention.

As indicated hereinabove, the compounds or agents which activate or inhibit ADPRT or which induce cellular or oxidative stress or which act as inhibitors or antagonists of calmodulin or $Ca^{++}$-calmodulin binding and the associated cytotoxic or cytostatic agent employed in combination therewith may be administered to the human patient undergoing treatment simultaneously, separately or combined in the same composition, or substantially simultaneously, such as one compound or agent before the other or within the period of time of 1–120 minutes, more or less, after administration of the first compound or agent of the combination. These administrations, usually intravenously, may be continued over an extended period of time of days, weeks or months.

Compositions in accordance with the practices of this invention which are usefully employed for inhibiting, controlling or reducing in humans the growth of human tumor or cancer cells by administration alone or in combination with radiation therapy contain an effective amount of a cytotoxic or cytostatic compound or agent in the range 0.1–20 parts by weight or mols and an effective amount of a compound or agent which activates or inhibits the chromatin-bound enzyme adenosine diphosphate ribosyl transferase ADPRT or which induces cellular or oxidative stress or which acts as an inhibitor or antagonist of calmodulin or $Ca^{++}$-calmodulin binding in the range 0.1–20 parts by weight or mols. The above-mentioned amounts of these compounds present in the compositions of this invention are relative to each other, i.e. for every 0.1–20 parts by weight or mols of one compound there is present a corresponding amount in the range 0.1–20 parts by weight or mols of the other compound.

Such compositions are administered by the usual or conventional techniques, e.g. orally, intramuscularly, intravenously or subcutaneously, usually depending upon the character of the cytotoxic or cytostatic compound present in the composition and the nature, amount and location of the tumor or cancer cells being treated. The amount or dosage of such compositions administered also depends upon the character of the cytotoxic or cytostatic compound in the composition as well as the character of the other compound making up the composition of this invention, the amount and/or nature of the tumor or cancer cells being treated and the extent or degree of inhibition of the tumor or cancer cells desired.

Although compositions in accordance with this invention usually contain a compound which activates or inhibits ADPRT in an amount in the range 0.1–20 parts by weight or mols, compositions which contain such compounds in an amount outside this range are also useful. For example, compositions which contain compounds which activate ADPRT in an amount in the range 0.01–12 parts by weight or mols or, for example, and amount in the range 0.5–2.0, are also useful. Compositions which contain these same amounts or ratios of the other compound, i.e. compounds which induce cellular or oxidative stress which act as inhibitors or antagonists of calmodulin or $Ca^{++}$-calmodulin binding are also useful in the practices of this invention.

Although emphasis in the disclosures of this invention has been placed on the use of these compositions for inhibiting in humans the growth of tumor or cancer cells, compositions of this invention which contain substantially only a compound or agent which induces cellular or oxidative stress or which acts as an inhibitor or antagonist of calmodulin or $Ca^{++}$-calmodulin binding, are also useful. For example, such special compositions in accordance with this invention which contain a compound or agent which induces cellular or oxidative stress or which acts as an inhibitor of calmodulin or $Ca^{++}$-modulin binding without a cytostatic or cytotoxic drug or with the substantial absence therein of a cytostatic and/or cytotoxic drug, are useful in the treatment of human patients undergoing radiation therapy for inhibiting the growth of tumor or cancer cells.

Indeed, in accordance with yet another embodiment of the practices of this invention such compositions which do not contain a cytostatic and/or cytotoxic drug are useful in the long term treatment of humans for the prevention of cancer. Such long term treatment would extend over a period of many months and years, with regular small dosages to the human patient of a composition in accordance with this invention which contains a compound or agent which induces cellular or oxidative stress or which acts as an inhibitor or antagonist of calmodulin or $Ca^{++}$-calmodulin binding. Such compositions when employed for long term treatment for the prevention of cancer in humans might also contain a small clinically ineffective amount of a cytotoxic or cytystatic drug. This aspect of this invention, however, for the prevention of human cancer is presently less preferred than the use of compositions which contain substantially only a compound or agent which induces cellular or oxidative stress or which acts as an inhibitor or antagonist of calmodulin or $Ca^{++}$-calmodulin binding.

As will be apparent to those skilled in the art in the light of the foregoing disclosures, many modifications, substitutions and alterations are possible in the practices of this invention without departing from the spirit or scope thereof.

What is claimed is:

1. A method of inhibiting or killing tumor or cancer cells in a human patient which comprises treating the patient with a chemotherapeutic agent or radiation while administering to the patient an N-substituted benzamide, that can activate ADPRT, in an amount effective to increase the cytotoxicity of the chemotherapeutic agent or the radiation.

2. A method according to claim 1, which comprises treating the patient with radiation while administering to the patient an N-substituted benzamide, that can activate ADPRT, in an amount effective to increase the cytotoxicity of the radiation.

3. A method according to claim 2, wherein said N-substituted benzamide, that can activate ADPRT, is metoclopramide.

4. A method according to claim 1, which comprises treating the patient with a chemotherapeutic agent while administering to the patient an N-substituted benzamide, that can activate ADPRT, in an amount effective to increase the cytotoxicity of the chemotherapeutic agent.

5. A method according to claim 4, wherein said N-substituted benzamide, that can activate ADPRT, is metoclopramide.

6. A method of inhibiting or killing tumor or cancer cells in a human patient which comprises treating the patient with a chemotherapeutic agent or radiation while administering to the patient, in combination, nicotinamide and an oxidative stressing agent in amounts that, in combination, are effective to increase the cytotoxicity of the chemotherapeutic agent or the radiation.

7. A method of inhibiting or killing tumor or cancer cells in a human patient which comprises treating the patient with a chemotherapeutic agent or radiation while administering to the patient (a) an N-substituted benzamide, that can activate ADPRT, in an amount effective to increase the cytotoxicity of the chemotherapeutic agent or the radiation or (b) in combination, nicotinamide and an oxidative stressing agent in amounts that, in combination, are effective to increase the cytotoxicity of the chemotherapeutic agent or the radiation.

* * * * *